US009393291B2

(12) United States Patent
Borodic et al.

(10) Patent No.: US 9,393,291 B2
(45) Date of Patent: Jul. 19, 2016

(54) USE OF BOTULINUM TOXIN FOR THE TREATMENT OF CEREBROVASCULAR DISEASE, RENOVASCULAR AND RETINOVASCULAR CIRCULATORY BEDS

(71) Applicants: Gary E. Borodic, Quincy, MA (US); Martin A. Acquadro, Wellesley, MA (US)

(72) Inventors: Gary E. Borodic, Quincy, MA (US); Martin A. Acquadro, Wellesley, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 248 days.

(21) Appl. No.: 13/862,206

(22) Filed: Apr. 12, 2013

(65) Prior Publication Data

US 2014/0105883 A1     Apr. 17, 2014

Related U.S. Application Data

(60) Provisional application No. 61/623,087, filed on Apr. 12, 2012.

(51) Int. Cl.
*A61K 38/48* (2006.01)
*A61K 9/00* (2006.01)
*A61K 47/42* (2006.01)

(52) U.S. Cl.
CPC ........... *A61K 38/4893* (2013.01); *A61K 9/0019* (2013.01); *A61K 9/0048* (2013.01); *A61K 47/42* (2013.01); *C12Y 304/24069* (2013.01)

(58) Field of Classification Search
None
See application file for complete search history.

(56) References Cited

U.S. PATENT DOCUMENTS

2009/0232850 A1* 9/2009 Manack et al. ............ 424/239.1
2009/0324647 A1* 12/2009 Borodic ..................... 424/239.1

* cited by examiner

*Primary Examiner* — Allison Fox
(74) *Attorney, Agent, or Firm* — Milbank, Tweed, Hadley & McCloy LLP (57) ABSTRACT

Methods of using botulinum toxin based pharmaceuticals are disclosed. The methods cause vasodilatation and decreased flow resistance of certain vascular beds for the purpose of increasing blood flow to a region in order to positively impact deterioration from a number of diseases.

18 Claims, 6 Drawing Sheets
(1 of 6 Drawing Sheet(s) Filed in Color)

Injection of botulinum toxin in the inguinal region for lower limb ischemia and caudication

Fig 4

Injection into the posterior popliteal artery with botulinum toxin for lower limb vascular insufficiency

USE OF BOTULINUM TOXIN FOR THE TREATMENT OF CEREBROVASCULAR DISEASE, RENOVASCULAR AND RETINOVASCULAR CIRCULATORY BEDS

This application claims the benefit of U.S. Provisional Application Ser. No. 61/623,087 filed on Apr. 12, 2012, the disclosure of which is incorporated herein by reference in its entirety.

FIELD OF THE INVENTION

Embodiments described herein deal with application of botulinum toxin based pharmaceuticals for the purpose of causing vasodilatation and decreased flow resistance of certain vascular beds for the purpose of increasing blood flow to a region in order to positively impact deterioration from a number of specified diseases. The cerebral arteriolar circulation is poorly assessable and often not adequately treated in low blood flow diseases such a generalized arterial sclerosis and stroke yet can be assessable by the process of deep diffusion of botulinum through the skull table. Other vascular beds for the treatment of low blood flow states are discussed in detail.

BACKGROUND OF THE INVENTION

New medical treatment methods utilizing pharmaceutical botulinum toxin formulations are disclosed herein.

SUMMARY OF THE EMBODIMENTS

In one embodiment, methods for increasing cerebral blood flow are disclosed. These methods include the identification of patients suffering from impaired cerebral blood flow (CBF), or patients at risk for developing impaired CBF; injecting botulinum toxin to the patients; allowing the botulinum toxin to spread within the deep brain struction to cause an increased CBF; and thereby preventing progression or enhancing the recovery from cerebrovascular disease. In certain embodiments the impairment to CBF includes or is caused by stroke, vascular bed development impairment, hypoxic ischemic encephalopathy, diabetes mellitus, carotid artery disease, aneurysm, hypertension, and/or Parry Rhomberg Syndrome.

In one embodiment a method for preserving intracranial cerebral blood flow in a patient prone to have an impairment in cerebral blood flow is disclosed. This may comprise steps of identifying a subject with high risk for impairment of cerebral blood flow or a patient who is at high risk for developing an impairment in cerebral blood flow; injecting a botulinum toxin preparation within a defined dose range into extracranial region of the head or neck; allowing the botulinum toxin to spread within the deep brain structure and cause increased cerebral blood flow; and thereby preventing progression or impairment from cerebral blood flow.

In one embodiment, a method of treating retinal vascular disease is disclosed. The method may comprise administering an intraocular injection of botulinum toxin at a predetermined dose through the pars plan into the vitreous body or aqueous humor to increase retinal blood flow to reverse or retard progression of disease. In some implementations, the injection includes high albumin preparations with ratio between units to albumin greater than 500 mcg/100 units. In some implementations, the retinal and ocular disease is low tension glaucoma. In some implementations, the ocular disease is advanced chronic open angle glaucoma.

In other embodiments, a method of treating congestive heart failure is disclosed. The method may comprise steps of using an aerosolized preparation of botulinum neurotoxin; delivering via nose, mouth or endotrachial tube or intra endrotracheal spray; allowing the botulinum to spread into both lungs; and wherein at least one measurement of congestive heart failure is improved.

In other embodiments, a method of treatment renal arterial insufficiency is disclosed. The method may comprise the steps of injection of botulinum toxin deep into lower thoracic and upper lumbar spine with long needle to place botulinum in close proximity to kidney. In some implementations, the arterial insufficiency is due to a diabetes mellitus.

In other embodiments, a method of treating caudication is disclosed. The method may comprise injection of botulinum toxin in region of the doralis pedis, femoral and popliteal arteries.

In other embodiments, a method of treating caudication using regional injection of botulinum toxin is disclosed. In some implementations, injections are given in region of the lower extremity lower extremity containing the major arteries governing blood flow. In some implementations, at least one symptom of the following conditions is improved: pain, exercise tolerance, distal extremity temperature, increased healing capacity of distal skin ulceration.

In certain embodiments, the methods may involve doses of 5-1,000 units of botulinum toxin.

BRIEF DESCRIPTION OF DRAWINGS

The patent or application file contains at least one drawing executed in color. Copies of this patent or patent application publication with the color drawing will be provided by the Office upon request and payment of the necessary fee.

DESCRIPTION OF EMBODIMENTS

Treatment of Cerebrovascular Insufficiency with Botulinum Toxin

Cerebrovascular Insufficiency and disorders of cerbrovacular blood flow are one of the most common problems in general medical practices. The condition can be associated with sudden onset due to vascular occlusion from a thrombic clot or emboli from a ruptured arteriosclerotic plaque, emboli from heart value, or a generalized form from multiple conditions causing narrowing of focal or diffuse arteriolar vascular beds in the brain structures contained in the neurocranium. Focal and generalized vessel disease may result from hypertension, metabolic conditions, generalized arterial sclerosis, diabetes, hyperlipidemia states, congenital vascular disease, structural intracranial vascular diseases. Morbidity includes effects from blockage of arteries and veins leading to death of brain tissue (stroke), resulting in paralysis, aphasia (speech loss and central impairment), blindness due to damage of the visual cortex and optic radiations, blindness due to retinovascular disease, numbness and dysesthesia due to involvement of sensory cortex or central nervous system sensory tracts, memory impairment due to global brain ischemia, memory impairment due to focal brain ischemia, generalized disorientation, short term memory loss, spatial recognition disorientation (agnosia), spasticity and facial palsy. Cerebral blood flow insufficiency to the brainstem and cerebellum can lead to truncal coordination, speech impairment, diplopia, slurred speech (dysphasia), in coordination of limbs, tremor, dystonia and facial sensory deficits.

Because of the risk of aggressive surgical intervention and the small dimensions of the cerebral arteries, placement of stents typically used to treat coronary artery disease can not be easily employed. Use of potent anticoagulants such as TPA have risks of intra cerebral hemorrhage and cannot be used on a chronic basis. Because of current therapeutic limitations, cerebrovascular insufficiency is generally not adequately treated yet remains one of the most common causes of morbidity from vascular diseases.

In certain embodiments, methods of using botulinum toxin based pharmaceuticals exist, for example, for injecting transcutaneously or by any of the routes of administration disclosed herein, to induce a central nervous system depressive effect for the treatment of various CNS (central nervous system) disorders. The inventor has found that botulinum toxin exerts a CNS effect in rats injected transcutaneously in the scalp. The injections are not intracranial or directly into the brain, but may include or specifically exclude intrathecal and intraspinal injection or administration. It is hypothesized and demonstrated that transcutaneous administration of botulinum toxin penetrates the blood/brain barrier. In certain embodiments, methods for using botulinum toxin based pharmaceuticals are disclosed herein for the treatment of seizures, anxiety, agitation, mania, bipolar disorders, generalized seizures, mental retardation, delirium, hyperactivity syndrome, attention deficit disorder (ADD), dementia, Huntington's disease, Alzheimer's disease, Parkinson's disease, psychosis, schizophrenia, insomnia and other CNS disorders. The specific mechanism now identified herein is a diffusion effect from extra-neurocranial injection which diffuses into the brain and selectively affects a vasodilatation of cerebral blood vessels allowing for a decrease in the flow resistance in the cerebrovascular bed and hence increased brain blood flow. Other applications involving the use of botulinum toxin for the treatment of vascular disease are disclosed.

Botulinum Toxin Diffusion into the Brain after Extracranial Injection.

Figure 1:
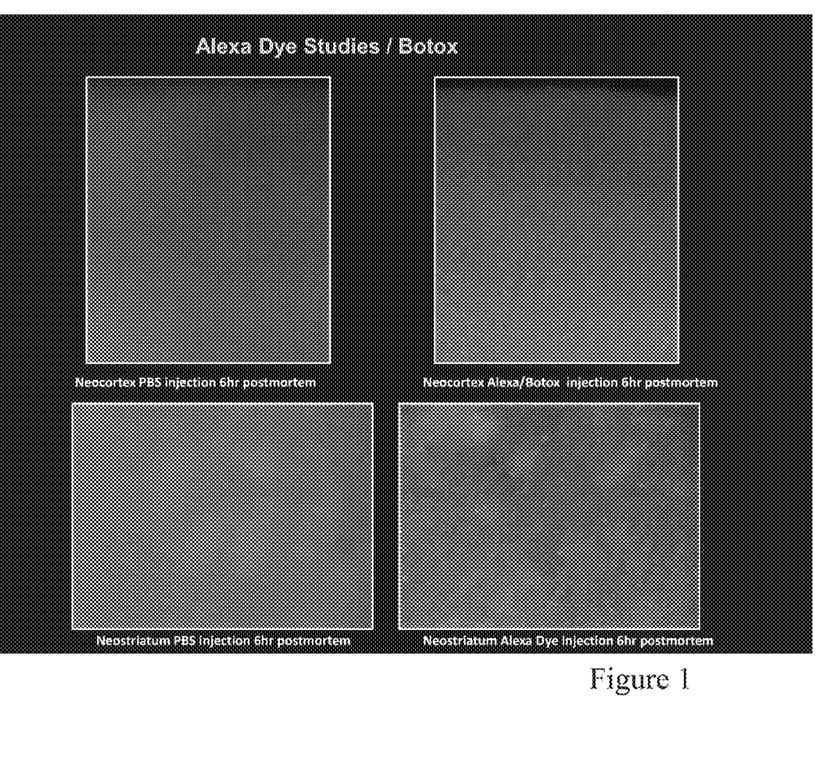
FIG. 1 depicts the fluorescence from Alexa dye in the brain at six hours after the injections and after animal sacrifice, at different intervals from 3 hours to 72 hours.

As ascribed herein the unexpected result of intercranial spread of botulinum toxin was demonstrated using histochemistry for neurotransmitters from extra neurocranial injections of botulinum toxin. Alterations in cholinesterase generation and neurotransmitter receptor expression was demonstrated as a result of subcutaneous injection in animal faces followed by subsequent brain cutting in the rodent model described herein. These findings were contrary to prior teachings that botulinum toxin at therapeutic levels did not cross the blood brain barrier. Alexa dye labeled botulinum toxin injected at higher doses was found to penetrate into deep tissues. Alexa dye staining of botulinum proteins is used for the fluorescence microscopy. Penetration into brain tissue was demonstrated post mortem in an animal model consisting of a 20 to 30 gram swiss Webster mouse in which the botulinum toxins were given over the frontal bone and periocular region followed by animal sacrifice and serial brain cutting analysis. After animal sacrifice, the serial brain cutting analysis was done at different intervals from 3 hours to 72 hours, which demonstrated the fluorescence from the Alexa dye in the brain at six hours after the injections (FIG. 1). The levels given to achieve this affect ranged from 10-50% fraction of the minimal lethal dose. It is clearly anticipated by the inventor and author that the therapeutic effective amounts will penetrate at much smaller levels given the high potency affect of the botulinum. Given the high degrees of safety profile generated by multiple clinical studies and clinical experience with botulinum toxin Type A, using botulinum toxin to access and create an effect on vessels in deep brain tissues is possible and one of the principle objects of certain embodiments disclosed herein. Other embodiments provide a method of vasodilation of deep, middle and small size arteries to decrease the vascular resistance and increase blood flow to damaged portions of the brain and hence achieve a beneficial affect. The method of injection could be under the skin, into the muscles under the periosteum, into nasal mucosa, into pharyngeal mucosa, mouth, tongue, facial sinuses, injected through the pars plana of the eye, into skull or other facial bones. All these injection sites are possible and have been used or anticipated in embodiments disclosed herein. These injections can prove to be effective, safe, without much risk of hemorrhage or substantial brain toxicity. The likelihood of neurocranial penetration of botulinum toxin is very high based on the laboratory experiments described herein and in this observation can be fashioned into an important therapeutic modality to produce a dose dependent diffusion gradient irrespective of limitations anticipated by the blood brain the blood brain barrier. The toxin injections can emanate into the brain via emissary vessels to the other tablet of the skull or possibly through the periocular and frontal region, facial region through retrograde venous drainage into the portal circulation of the base of the brain. The mechanism differs from prior theory of penetration via retrograde axoplasmic flow.

The vessel walls of the brain and other select vessel beds contain both cholinergic innervations and adrenergic innervations. Generally adrenergic innervations causes an intense vasospasm and if excessively stimulated could aggravate ischemia. In certain sates such as hypertension, adrenergic stimulation may be protective avoiding brain edema. Cholinergic innervations (acetyl choline driven neurotransmitter effect) is often been described by researchers as causing a vasodilatation which might improve circulation to the target region. Because of this past observation on cholinergic effects on blood vessels, it may seem contrary and counter intuitive that an anti-cholinergic such as botulinum toxin can produce a beneficial effect on blood flow to certain vascular beds. Although the adrenergic ganglia corresponding to the innervations of vessels in the brain are thought to be primarily driven by stellate ganglia, the injection locations advocated in embodiments herein do not solely call for injections into the region of adrenergic ganglia. In fact, the embodiments described herein call for injections anatomically away from adrenergic ganglia injections in the neck to produce the desired effect of increased cerebral blood flow by direct effect of cholinergic and possible adrenergic transmission on vessels within the neurocranium.

Cerebrovascular Injections with Botulinum Toxin.

Botulinum toxin has been previously demonstrated to have a relaxing affect on smooth muscle. Such an affect was noted in the bladder in the treatment of prostatic obstruction, spinal cord related injury, bladder outlet syndrome, benign prostatic hypertrophy, and bladder wall smooth muscle such as used to treat interstitial cystitis. Recently the use of vascular smooth muscle dilation has been a mechanism by which the toxin has been used to increase digital blood flow in patients with Raynaud's syndrome from a primary or secondary cause.

Botulinum toxin neurotoxin presumably blocks a sympathetic innervations of the digit vessels which relieves vasospasm and allows adequate blood flow to the digits essentially preserving the integrity of the fingertips in patients afflicted with these forms of disorders.

Low risk injection delivery of botulinum toxin to assess neurocranial vessels has enormous utility on being able to affect the small diameter intracranial vessels or even mid size vessels without causing damage to brain parenchyma. Brain parenchyma has not been damaged with large clinical studies of high dose botulinum toxin for the treatment of headache syndromes, spasmodic torticollis, facial nerve lesions such as Bell's palsy, hemifacial spasm, blepharospasm, sweating disorders of the face, head and neck region. Embodiments herein are dependent on diffusion into the deep neurocranium either through direct molecular dose related diffusion through bone, interstitial fluids or through possible hematogenous mechanism with venous drainage from the scalp, facial region or peri nuchal region. Doses of botulinum toxin can be quantitated using the LD 50 method or a diffusion quantization method, SNAP 25 bioassay, assay which measures both botulinum toxin receptive binding and SNAP 25 assays and other forms of neuronal cell based assays. The dose efficient to achieve an intracranial affect can range from 20 to 200 units, 200 to 2000 units or over 4000 units. The units of botulinum toxin are not universal and may depend on formulation, assay method, strain type, excipient composition and immuno type. All of these factors need to be considered in dosing and quantitation is possible when in a given formulation of botulinum toxin. This is proven to be a safe method of quantitation so that systemic botulinum poisoning does not occur with the injections. Quantization of an intracranial dose can be accomplished by observation of affects on cerebral blood flow using MRI technology, Doppler ultrasound technology, use of MR perfusion technology or any other method that determines cerebral blood flow. Technetium scans have also been used for nuclear medicine.

Target populations and indications, which can be treated, can contain high risk factors for cerebrovascular disease. Prophylactic treatment can be anticipated in categories which patients who have increased risk of cerebrovascular disease. These include:
  A) Diabetics with history of cardiac or coronary artery disease or peripheral vascular disease.
  B) Hypertensive patients with documented peripheral artery disease or coronary artery disease.
  C) Patients with proven carotid artery stenosis.
  D) Patients experiencing transient ischemic attacks or having had small strokes.
  E) Patients with evidence of narrowing of the vessels on computerized tomography, angiography, or magnetic resonance imaging.
  F) Patients with evidence of ocular ischemic disease, diabetic retinopathy or emboli in the retina.
  G) Patients with diabetes or diabetic macular edema, diabetic retinal neovascularization.
  H) Patients with Parry Romberg Syndrome, systemic lupus or any other collagen vascular disease.
  I) Patients with developing vascular dementia from small focal infarcts of the brain.
  J) A combination of risk factors as well can be important such as patients who have history of coronary artery disease or stroke, patients at high risk because of blood fat analysis, blood pressure, sex, smoking habits, exercise pattern, and cardiac arrhythmias.
  K) Patients with high risk of cognitive deterioration because of age.

Cerebrovascular Injections with Botulinum Toxin

The method of injection will depend on the target or region of the brain, which a maximal effect would be desirable to achieve. The region can be localized based on neuroimaging analysis of the brain using any of the above methods, could also be based on a developmental past medical history or neurologic exam. The region can be localized to a hemisphere, which we require multiple injections over bone corresponding to the targeted hemisphere. It could also be localized to a region of the brain, which the maximal toxic affect would be desirable to achieve. For instance, a patient diagnosed as having epilepsy from vascular insufficiency to the temporal lobe, may receive an injection over multiple regions over the temporal bone. A patient who has a loss of vision for occipital cortex could receive injections over the occipital bone corresponding to the occipital visual cortex. The patient with a brainstem stroke or brainstem cerebrovascular insufficiency may be injected in the peri orbital, nasal region, or oropharynx to achieve the necessary affect. For ocular affects, peribulbar or subconjunctival injections can be used, transocular injections over the pars plana into the vitreous gelatin can be used and the fashion commonly used today to inject Avastin for the treatment of macular degeneration. It is anticipated that careful analysis of blood flow affects and clinical affects would be analyzed to determine the duration of affect and the degree of dosing that would be required. The degree of dosing would fall within categories in realms that have been previously used and proven to be safe for the body region injected.

The dose can be from 10-1500 units dependent on body size, weight, and respiratory status. Various immunotype A-G may be used, but preferably type A is associated with highest potency. Injections may be placed in close proximity to the internal carotid artery to achieve maximum dilation of this major artery to the brain or over the cerebral vertebra which houses the vertebral foramen, which houses the vertebral arteries, which perfuse the posterior portion of the brain. Injections around the neck and carotid artery can be given in the region of the stellate ganglion, which effectively creates a stellate ganglion block as an additional affect to the adrenergic block causing blood vessel dilation.

Cerebrovascular Embodiments Summary

Embodiments described herein are practiced based on identifying a patient with an impairment of CNS blood flow using diagnostic techniques and physician signs and symptoms to establish a nosologic diagnosis.

Cerebral flow studies may be accomplished with perfusion MRI, spectral MRI, Doppler studies (Doppler ultrasound), PET scanning, laser Doppler, radionucleotide studies using various isotopes (e.g. SPECT scanning), or any other method to establish and quantitate cerebral blood flow. The establishment of cerebrovascular disease may also be based on structural studies based on various forms of angiography (CT angiography, MRA, other forms of imaging tests). Identification of subjects may also be solely accomplished by clinical examinations eliciting history of signs and symptoms, neurologic examination for sensory movement memory, spatial orientation, visual field, eyesight, coordination and balance, facial expression, or other signs and symptoms on neurologic exam and medical history.

Once the subject is identified, the goal is established for neurotoxin administrations. This goal may be prophylactic to prevent cerebrovascular disease in a high risk population for the development of cerebrovascular disease, prevent cognitive deterioration because of excessive age, or for prophylaxis in a subclinical cerebrovascular lesion based on brain imaging for other purposes. Other goals may be to enhance recovery of central neurologic function after stroke, brain traumatic injury, immunologic vascular diseases, neonatal diseases involving impaired blood flow (perinatal stroke, periventricular leukomalacia, perinatal hypoxic-ischemic encephalopathy), Parry Rhomberg syndrome, scerloderma, cerebral palsy prevention, cognitive congnitial impairment prevention, intracerebral hemorrhage related vasospasm, aneurysm, cerebral vasculitis, hypertension, diabetic related encephalopathy, central nervous system lupus, sarcoidosis, hyerplastic congenital carotid artery disease, arteriosclerotic Alzheimers disease, moya disease, degenerative CNS disease associated with impaired blood flow or other conditions associated with impaired cerebral blood flow. The object of certain embodiments is to preserve central nervous system function after vascular compromise or insult with both preventive and/or rehabilitation goals. Clinical studies analysis data is helpful in establishing specific patient diagnosis and subsets which may prove more responsive.

In neonates vascular bed mal-development is associated with peri ventricular leukomalacia and hypoxic ischemic encephalopathy which are causes of cerebral palsy and congenital intelligence disorders, congenital cognitive disorders, hearing disorders, speech disorders, congenital visual disorders, mental retardation, ataxia, and dystonic movements.

The injections given or established based on dose, immunotype; area of brain targeted, and cycle timing. Doses should be given which clearly do not exceed toxin spread levels. Levels of spread can be assessed physically or using electromyography. Once the extracranial injection is accomplished, post injection monitoring may be done with both subjective and objective methods assessing cerebral blood flow. Repeated injections are necessary to maintain effects. Dosing ranges can vary but are between 10-15,000 LD 50 units dependent on the immunotype or formulation used. Immunotype A (or any Clostridial species producing variants of immunotype A showing higher potency), or immunotype B-G. Various excipient formulations which may enhance diffusion into the neurocranium are contemplated with alteration in excipient protein composition, lowered pH, or use of spread enhancing enzymes' such as hyaluronidase.

Repetitive injections over a lifetime may be given as safety factor and low immunogenicity of preparations are now established. The injection sites may be chosen to include both areas more likely to enhance brain penetration such as supraorbital regions, sinuses, nasal mucosal areas, or areas which may impact autonomic sympathetic innervations of vessels such as neck region (stellate ganglion) or other regions of autonomic ganglia.

Ophthalmic Administration for Retinal and Intra-Ocular Vasculopathy

Intraocular vasculopathy is a major cause of blindness. Diabetic retinopathy is the leading cause of blindness in the middle age population and occurs as a result of leakage of retinal circulation (macular edema), neovascularization from the growth of new blood vessels and vascular occlusion. The condition is insidious and often progressive. Despite use of laser and anti-VEGF agents, disease can progress to blindness from vascular occlusive or from complications relating to the growth of new blood vessels on the retina which leads to fibrosis and retinal detachment. Increasing blood flow has the advantage of decreasing ischemia and retarding new blood vessels formation and therefore mitigating this complication. Although it may seem that increasing the blood flow to the eye could damage a retina with pre-existing endothelial compromise, the contrary result endures because the stimulus for vascular damage is blood flow.

Other causes of intraocular vasculopathy are central retinal artery and central retinal vein occlusion. Here loss of retinal nerve fiber layer from arterial and venous occlusion leads to loss of retinal tissue with resultant loss of vision. Here vasodilatation is needed al to protect further deterioration of inner and outer retina so that maximal recovery is possible.

Other causes of visual loss are retinopathy of prematurity, condition which is associated with poor retinal blood flow from a partially incomplete retinal vasculature. Here the lack of a fully developed retinal circulation results in temporal or peripheral retinal disease, scar formulation and tractional retinal detachment. Use of improved methods to maintain retinal blood flow can sustain perfusion and mitigate against this complication after intra ocular injection.

Other Causes of retinal vasculopathy is various hemoglobinopathies, particularly sickle cell disease, a condition of persons of African dissent. Here the loss of blood flow is due to a condensation of hemoglobin within the cells cause microscopic perfusion defects and loss of optic nerve and retinal blood flow with all the attendant effect thereof. Increasing perfusion can be helpful in sustaining retinal health.

Ischemic optic neuropathy from idiopathic and arteritic cause can also be targeted.

Another cause of visual loss includes low tension glaucoma in which the intra-ocular pressure is maintained however the afflicted continues to loss visual filed which can ultimately led to blindness. Here the afflicted can complain of transient loss which heralds further permanent visual loss. Because of the association of this condition with vasospastic disease, the use of botulinum toxin is effective when injected intra-ocular through the pars plana. Additionally advanced stages of chronic open angle glaucoma suffer vascular compromise and use of botulinum can be used to foster neuro protection, limiting deterioration of vision when intra ocular pressure control is maintained.

Other causes impaired blood flow included various forms of vasculitis including sacoidosis, uveitis, microemboli, and carotid occlusion. Extra ocular injections may be given to foster lower intensity neuroprotection.

In most of the above ocular applications, delivery of botulinum toxin should be by pars plana injection method directly into the vitreous body to allow the highest concentration of botulinum toxin which diffuses into the retina or choroid without peripheral diffusion from injection site. The needle size is between 25-35 gauge. Dose can be from 0.5-2000 U, depending on formulation or immunotype used.

Care is made not to give enough toxin to allow diffusion outside the eye to effect weakness of the extra-ocular muscles and cause mal alignment of the eyes and disruptions of extra-ocular movement.

It should be noted that certain retinal degenerations such as retinitis pigmentosa and various forms of progressive myopia are associated with attenuated narrowing of the retinal vascular circulation. Vasodilatations in such condition can function to preserve and retard neurodegeneration and therefore proved useful in preserving vision.

Use of Botulinum Toxin to Treat Congestive Heart Failure

Paradoxically, botulinum toxin, a strong relaxant of muscle, can be used to treat congestive heart failure by reduction in peripheral vascular resistance in key regional circulatory systems. Congestive heart failure is one of the most common diseases affecting the elderly and results from a number of causes the flowing table outlines causes of congestive heart failure:
1. Coronary artery disease
2. Hypertension
3. Valvular heart disease 4. Myocarditis
5. Cardiomyopathy
6. Abnormal rhythms
7. Anemia
8. Hyperthyroidism
9. Amyloidosis
10. Hypothyroidism
11. Pulmonary embolism
12. Sarcoidosis
13. Restrictive cardiomyopathy (Rheumatoid disease and Parvovirus disease)

The mechanism of action is reduction in peripheral resistance in peripheral arterial resistance in critical regional circulations by reduction in adrenergic tone and vasodilatation. Congestive heart failure is often treated by cardiac unloading agents with cause's vasodilatation in arteries and veins effectively reducing the amount of pressure and resistance which influences cardiac work and output. Drugs such as lisinopril accomplish this goal by functioning as a angiotension converting enzyme inhibitor which effectively block the generation of active angiotension II, a potent vasoconstrictor which relieve heart failure. Further effects on brakykinin also serve to promote vasodilatation and cardiac unloading. Similar properties of botulinum toxin can be used to alter regional blood flow the pulmonary circulation to relieve right sided heart failure and to certain regions of the systemic arterial circulation to relieve left sided heart failure. The administration to the pulmonary circulation can be by aerosol by oral nasal or pressure controlled (CPAP) devices and to the systemic circulation by injection in regions with vascular beds such as the peri-nephric area via long needle injections in the paraspinal muscle area or deeper into the perinephric capsule.

Pulmonary Hypertension

Pulmonary arterial hypertension; Sporadic primary pulmonary hypertension; Familial primary pulmonary hypertension; Idiopathic pulmonary arterial hypertension; Primary pulmonary hypertension; PPH; Secondary pulmonary hypertension Pulmonary hypertension is abnormally high blood pressure in the arteries of the lungs. It makes the right side of the heart need to work harder than normal.

The right side of the heart pumps blood through the lungs, where it picks up oxygen. Then, the blood returns to the left side of the heart, where it is pumped to the whole body.

When the small arteries (blood vessels) of the lung become narrowed, they cannot carry as much blood. When this happens, pressure builds up. This is called pulmonary hypertension. The heart needs to work harder to force the blood through the vessels against this pressure. Over time, this causes the right side of the heart to become larger. Not enough blood flows to the lungs to pick up oxygen. At this point, heart failure involves the right side of the heart. This is called cor pulmonale. Pulmonary hypertension may be caused by:

Autoimmune diseases that damage the lungs, such as scleroderma and rheumatoid arthritis Birth defects of the heart
Blood clots in the lung (pulmonary embolism)
Congestive heart failure
Heart valve disease
HIV infection
Low oxygen levels in the blood for a long time (chronic)
Lung disease, such as COPD or pulmonary fibrosis
Medicines (for example, certain diet drugs)
Obstructive sleep apnea In many cases the cause is unknown. In this case, the condition is called idiopathic pulmonary arterial hypertension (IPAH). It used to be called primary pulmonary hypertension (PPH), IPAH is rare. It affects more women than men.

If pulmonary hypertension is caused by a known medicine or medical condition, it is called secondary pulmonary hypertension Shortness of breath or light-headedness during activity is often the first symptom. Fast heart rate (palpitations) may be present. Over time, symptoms occur with lighter activity or even while at rest. Other symptoms include ankle and leg swelling, bluish color of the lips or skin (cyanosis), Chest pain or pressure, usually in the front of the chest, Dizziness or fainting spells, Fatigue, Weakness People with pulmonary hypertension often have symptoms that come and go. They report good days and bad days.

A physical examination may show abnormal heart sounds, feeling of a pulse over the breastbone, Heart murmur on the right side of the heart, Larger-than-normal veins in the neck, Leg swelling, Liver and spleen swelling. In the early stages of the disease, the exam may be normal or almost normal. The condition may take several months to diagnose. Asthma and other diseases may cause similar symptoms and must be ruled out. Tests useful to confirm the diagnosis include
Blood tests
Cardiac catheterization
Chest x-ray
CT scan of the chest
Echocardiogram
ECG
Lung function tests
Nuclear lung scan
Pulmonary arteriogram
Six-minute walk test
Sleep study There is no known cure for pulmonary hypertension. The goal of treatment is to control symptoms and prevent more lung damage. It is important to treat medical disorders that cause pulmonary hypertension, such as obstructive sleep apnea, lung conditions, and heart valve disorders.

Many new treatment options for pulmonary arterial hypertension (IPAH) and other forms of pulmonary aterial hypertension are becoming available. Medicines used to treat pulmonary hypertension include:
Ambrisentan (Letairis)
Bosentan (Tracleer)
Calcium channel blockers
Diuretics
Prostacyclin or similar medicines
Sildenafil and similar medicines Some patients are put on blood thinners to reduce the risk of blood clots in leg veins and lung arteries. People with low oxygen levels in the blood may need oxygen therapy at home. As the illness gets worse, you will need to make changes in your home and get more help around the house.

If treatment with medicine does not work, a lung or heart-lung transplant may help some people.

The long-term outlook has been poor, but new treatments may lead to better results. Some people with this condition may have heart failure that could lead to death.

It is not a good idea to get pregnant if you have this condition.

Use of botulinum toxin would be accomplished via a nasal oral or CPAP spray into the lungs. This method ironically has been the technique in formulating botulinum toxin as an germ weapon agent and references on formulation regarding this use in referenced herein. Aerosolized dosing will vary from 20-2000 units based on LD 50 assay techniques, formulation, immunotype and cell bank from C botulinum used. Various surfactants may be used in the formulation. The aerosol shall be titrated against pulmonary function tests measuring tidal volume, forced expiratory volume (FEV1) and other pulmonary function tests, exercise testing, oxygen saturation, arterial pO2, pCO2, chest expansion and diaphragm movement. Under certain circumstances, use of central venous pressure, pulmonary wedge pressure, and pulmonary arterial pressure can be measured for titration purposes. Monitoring pulmonary artery flow via ultrasound Doppler techniques may also be used. Evaluating peripheral edema, patients weight, orthopnea, venous blood flow in neck may also be endpoints for monitoring pharmacologic effects.

Figure 2:
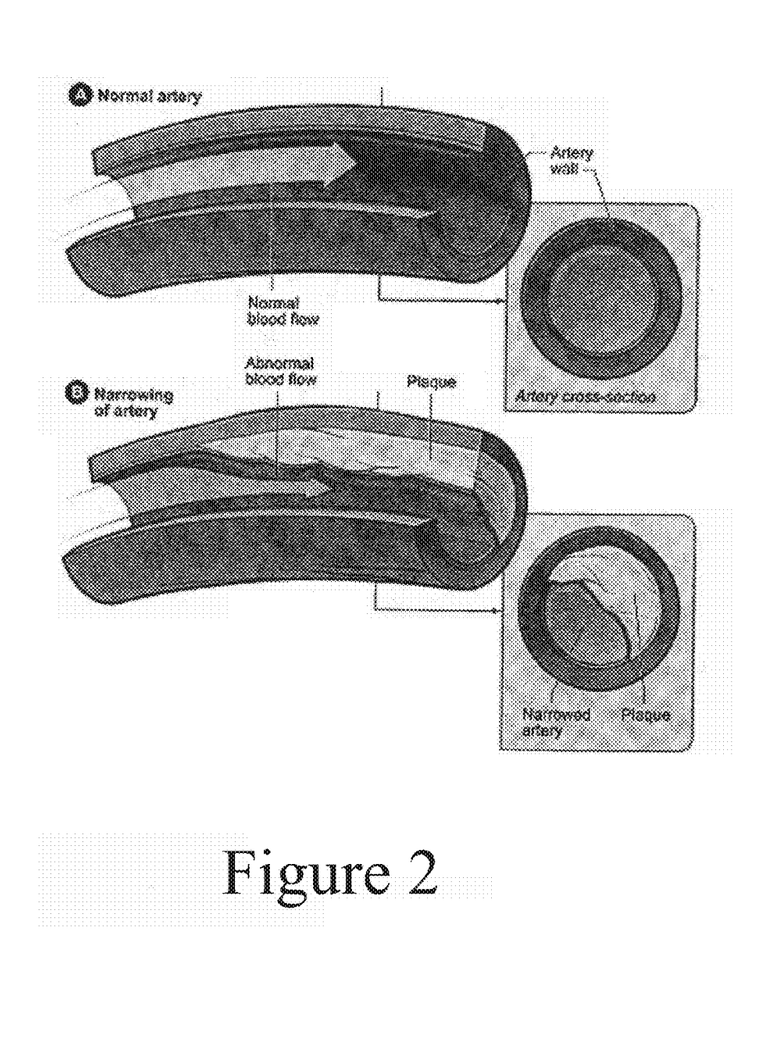
FIG. 2 depicts the renal vascular bed.

Renal Vascular Bed (See FIG. 2)

Because the kidney is located in the retroperitoneal space the organ is assessable by paraspinal muscle injection using a deeply penetrating needle over the thoracic and lumbar spine. The kidneys are involved heavy in fluid dynamics and regulation of the circulatory system by sodium retention, intravascular volume via generation of pressor hormone such as rennin, angiotenson, and sodium retention hormones. Many of these responses are autonomically and in particular adrenergically mediated. Inc congestive heart failure, poor perfusion to the kidney can aggravate sodium retention and therefore worsen the heart failure. Furthermore poor renal perfusion can damage glomerular structures and further lead to fluid retention. Denervating the kidney can serve to mitigate these effects and well as serve to preserve renal parenchyma during low perfusion states. The botulinum toxin injections are given with long needle through paraspinal muscles into deep muscles outside the renal structure. By dose adjustment, the perfusion effect can be accomplished to improve blood flow to the kidneys. The injections can be given repetitively to maintain the effect.

Measured blood flow can to accomplished with Doppler ultrasound, radio nucleotide scanning, measurement of certain hormones, urine output, patient weight, blood urea nitrogen measurements, creatine blood measurements, and electrolyte measurements.

Causes of Renal Vascular Insufficiency are as Follows:

The most common causes of CKD are diabetes mellitus, hypertension, and glomerulonephritis. Together, these cause approximately 75% of all adult cases. Certain geographic areas have a high incidence of HIV nephropathy.

Historically, kidney disease has been classified according to the part of the renal anatomy that is involved:

Vascular, includes large vessel disease such as bilateral renal artery stenosis and small vessel disease such as ischemic nephropathy, hemolytic-uremic syndrome and vasculitis Glomerular, comprising a diverse group and subclassified into Primary Glomerular disease such as focal segmental glomerulosclerosis and IgA nephritis Secondary Glomerular disease such as diabetic nephropathy and lupus nephritis Tubulointerstitial including polycystic kidney disease, drug and toxin-induced chronic tubulointerstitial nephritis and reflux nephropathy Injections for the treatment of renal disease may be accomplished from the back with long needles to allow diffusion into the kidney region and its vasculature.

Injections can be used to mitigate progression of nephritis, glomerulonephritis, glomerculonephritis, diabetic nephropathy, hypertensive nephropathy, renal artery stenosis, renal vasculitis, or any other disorder involved with vascular compromise.

Injections may help retard congenital renal disease progression.

Dosing is from 20 U—10,000 per kidney dependent on immunotype and formulation used and injections will need to be repetitively administered.

Caudication.

Figure 3:
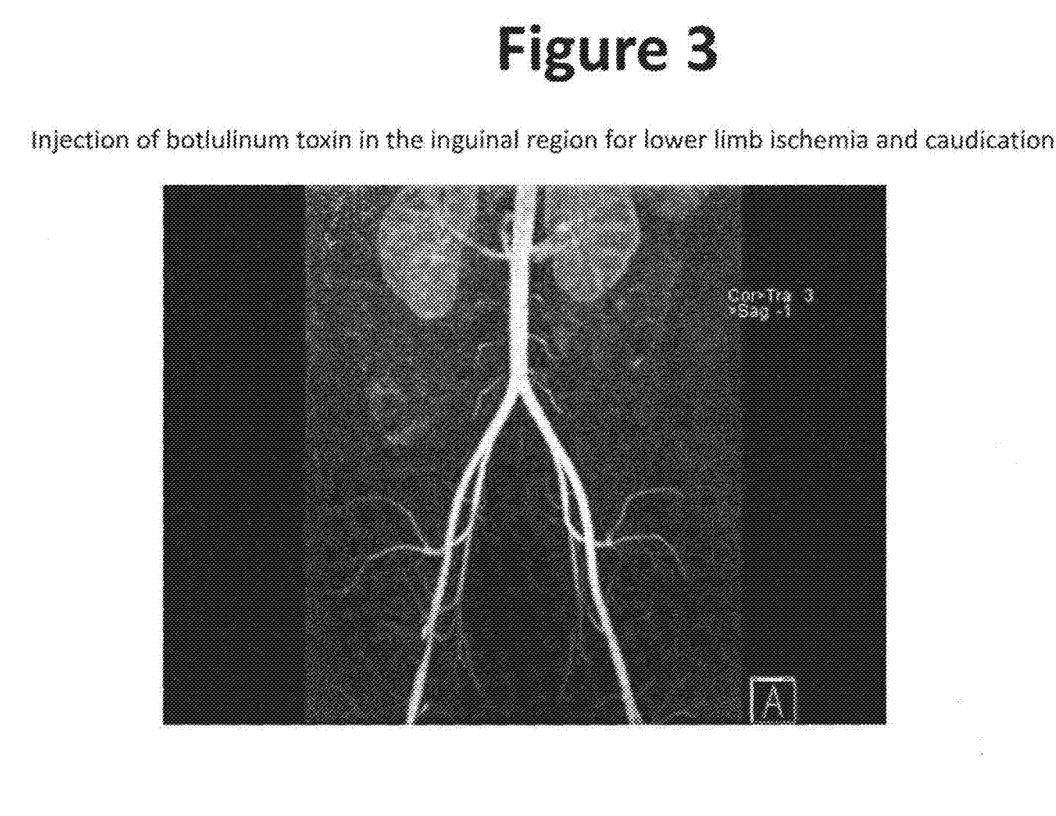
FIG. 3 depicts injection of botulinum toxin in the inguinal region for lower limb ischemia and caudication.

Caudication is a team which refers to pain in the legs with significant activity which is caused by atherosclerotic blockages of the arteries of the leg. Typically patients have a crampy pain in their legs after a certain amount of exercise. This pain usually goes away after a few minutes of rest. FIG. 3 depicts injection of botulinum toxin in the inguinal region for lower limb ischemia and caudication.

Claudication symptoms include:

Pain when exercising. You may feel pain or discomfort in your feet, calves, thighs, hips or buttocks depending on where you might have artery narrowing or damage. Claudication can also occur in your arms.

Intermittent pain. Your pain may come and go as you do less-strenuous activities.

Pain when at rest. As your condition progresses, you may feel pain in your legs even when you're sitting or lying down.

Discolored skin or ulcerations. If blood flow is severely reduced, r toes or fingers may look bluish or feel cold to the touch. Sores can develop on the lower legs, feet, toes, arms or fingers.

Claudication is another condition caused by atherosclerosis, a buildup of plaque in the arteries of the body. This time, the plaque build up occurs in the arteries of the legs, or the arteries leading to the legs. In most cases, patients don't have pain without activity, but when they walk, and more blood is required to deliver oxygen to the tissues, their narrowed vessels are unable to deliver the required blood flow, and pain ensues. Therefore, when activity is stopped, blood is again delivered in adequate amounts to the tissues, and the pain goes away.

Symptoms

Claudication is discomfort or pain in your legs that happens when you walk and goes away when you rest. You may not always feel pain; instead you may feel a tightness, heaviness, cramping, or weakness in one or both of your legs. Claudication often occurs more quickly if you walk uphill or up a flight of stairs. Over e, you may feel claudication at shorter walking distances, as the degree of artery blockage worsens.

Causes

Claudication is a symptom of peripheral arterial disease (PAD), which is caused by atherosclerosis. Therefore, the factors which increase the risk for atherosclerosis are the same as those which increase the risk for claudication. Risk factors for atherosclerosis include:

Smoking

High cholesterol levels in the blood

High blood pressure

Obesity

Having a family history of heart or vascular disease

Tests

One of the most important ways that claudication is diagnosed is with a good history and physical exam. Other types of pain can mimic claudication, so it can sometimes take an experienced vascular surgeon to determine whether or not claudication is indeed present.

After your exam, if we suspect PAD and claudication, other tests may be ordered, such as:

Ankle-brachial index (ABI), which compares the blood pressure in your arms and legs.

Pulse volume recording, which measures the volume of blood at various points in your legs.

Duplex ultrasound which shows blood flow in the blood vessels in the leg, and can detect the location and number of specific narrowings.

Blood tests for cholesterol, high blood sugar or other markers for artery disease.

Magnetic resonance angiography (MRA), which is an advanced MRI which can show the blood vessels in the legs.

Computerized tomographic angiography (CTA), which is an advanced CT scan which can generate pictures of your blood vessels in 3D.

Angiography, a more invasive procedure where the arteries are injected with dye and pictures are obtained.

Past Treatment

PAD is a very serious condition because it indicates that significant atherosclerosis is present in the body. Remember, atherosclerosis is the condition that most often leads to serious and deadly conditions like heart attacks and stroke!

Therefore, we take PAD very seriously, and work with patients to strictly control their risk factors for atherosclerotic disease. We aggressively treat high blood pressure, diabetes, and high cholesterol. We help you with a real plan for regular exercise and a healthy diet, often referring you to a dietician when needed. If you are a smoker, we work with you to stop smoking at all costs. When appropriate, we test you for other conditions, such as aortic aneurysms, carotid artery disease, and heart disease, so we discover these conditions and treat them before they become dangerous. We add medications which are known to be beneficial in patients with PAD, such as aspirin and plavix in certain patients. Exercise therapy/smoking cessation may help.

Treatment of claudication and peripheral artery disease can help prevent the disease from getting worse and reduce symptoms. Lifestyle changes, such as quitting smoking and participating in a regular exercise regimen, are often the first steps in treating claudication.

If your claudication symptoms don't improve with conservative efforts, other treatment options include:

Medications. Aspirin to reduce the chance of blood clots. Similar medications include clopidogrel (Plavix), dipyridamole (Persantine) and ticlopidine. The medication cilostazol (Pletal) pentoxifylline (Trental) may help improve blood flow and reduce symptoms Angioplasty. Cases of claudication and peripheral artery disease that are more serious may require angioplasty. This is a procedure that widens damaged arteries using a narrow tube that travels through your blood vessels and has an inflatable balloon on the end that can help improve circulation. A stent is often implanted at the same time to keep the artery propped open. Once an artery is open, a small metal or plastic mesh tube (stent) in the artery to keep it open.

Vascular surgery. Surgery that takes a healthy blood vessel from another part of the body to replace the vessel s causing claudication. This allows blood to flow around the blocked or narrowed artery. Various synthetic bypass tubes may also be considered and substituted for vessel autographs.

Use of Botulinum Toxin to Treat Caudication and Symptoms of Peripheral Arterial Disease:

Botulinum toxin can be used to treat caudication by effecting a block in adrenergic and other autonomic stimulation of the blood vessels of the legs. The effect may be directly on smooth muscle or smooth muscle innervations with cholinergic transmission. The effect is to cause vasodilatation, decreased vascular bed resistance and increased blood flow and improvement of lower limb function with mitigation of lower limb pain with exertion. The anatomy of the lower leg is conducive to this approach as the femoral arterial is superficial in the region of the inguinal ligaments, the tributary popliteal artery is superficial to the back of the leg and the further tributaries the dorsalis pedis and posterior tibeal arteries are superficial in the feet. The anatomic location and the lends for easy access to botulinum toxin injections at does between 5-15,000 LD 50 units from various formulations and immunotypes of botulinum toxin in these regions which can be used to relieve symptoms of caudication by increasing blood flow to the lower extremity. Injections in the region of the pelvic plexus may be useful to create further chemo sympathectomy to increase blood flow and therefore relieve symptoms.

Botulinum toxin may be used for caudication because of its effect on smooth muscles and effect on promoting blood flow to the lower extremities. The vessel wall of the lower extremity has both cholinergic innervations and adrenergic innervations. Generally adrenergic innervations causes an intense vasospasm and if present would aggravate caudication. Cholinergic innervations (acetyl choline driven neurotransmitter effect) is often been described by researchers as causing a vasodilation which might improve circulation to the lower extremity. Because of this past observation on cholinergic effects on blood vessels it may seem contrary and counter intuitive that a anti-cholinergic such as botulinum toxin can produce a beneficial effect on blood flow to the lower extremity as advocated. Although the adrenergic ganglia corresponding to the innervations of vessels in the lower extremity are thought to be primarily driven by cholinergic neurotransmitters, the injection locations advocated in certain embodiments herein do not solely call for injections into the region of adrenergic ganglia. In fact, embodiments described herein call for peripheral peri arterial injections away from adrenergic ganglia to produce the desired effect of increased lower extremity blood flow.

Figure 4:
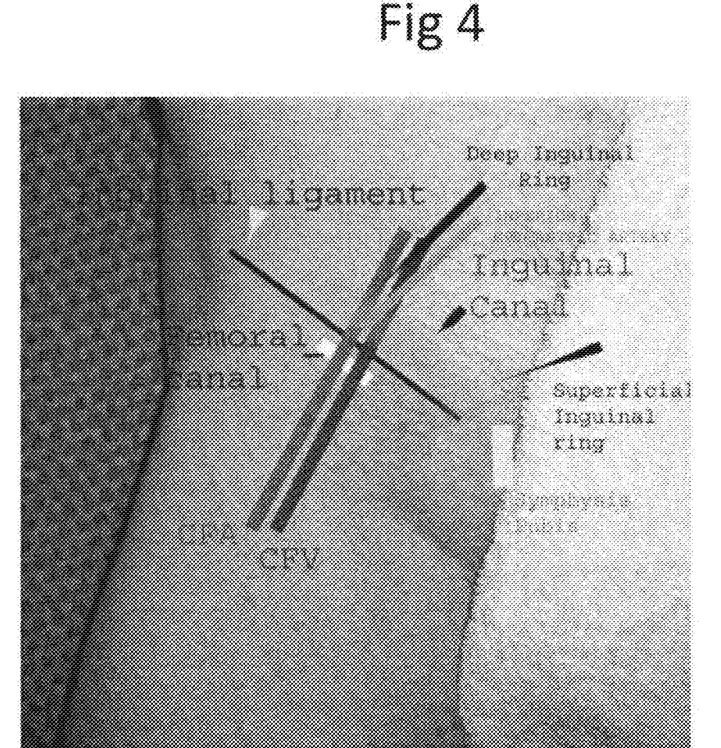
FIG. 4 depicts the femoral region corresponding to the area around the inguinal ligament (femoral artery).
Figure 5:
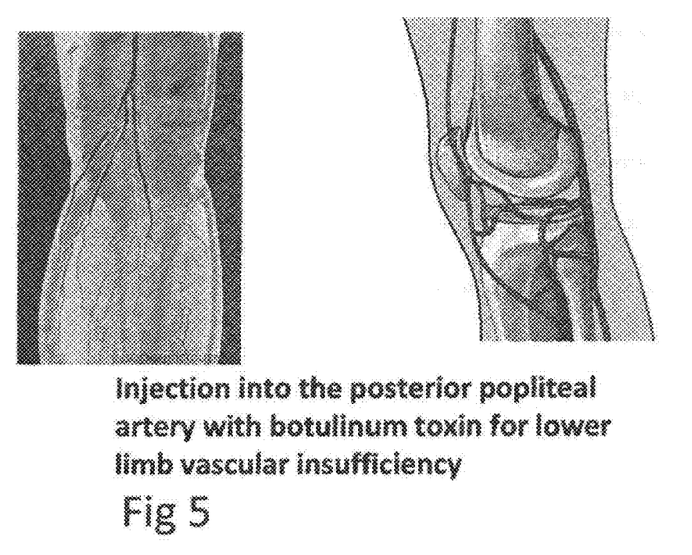
FIG. 5 depicts the popliteal region in the back of the knee (Popliteal artery).
Figure 6:
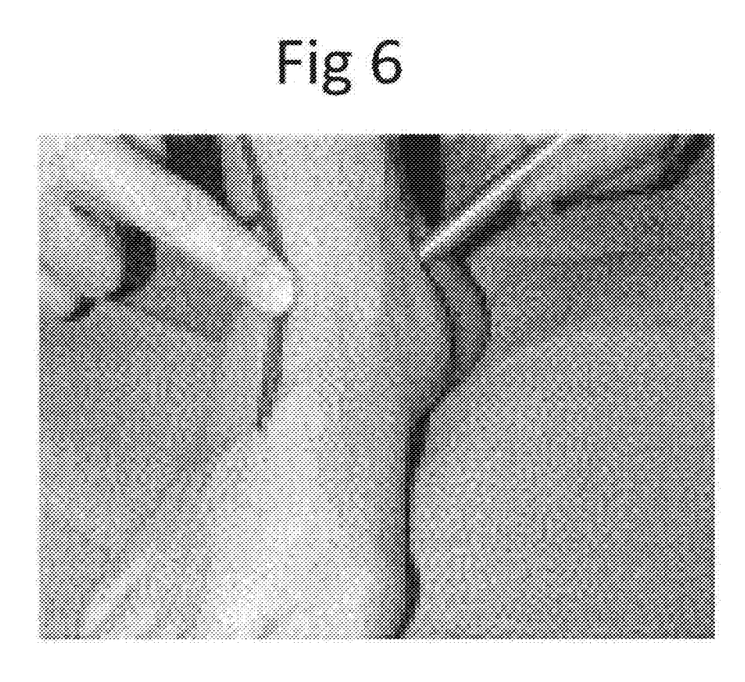
FIG. 6 depicts the foot region instep (dorsum) and medial posterior tibial. (Corresponding to the posterior tibial artery).

Summarizing certain embodiments, the blood supply to the lower extremity is primarily mediated by tributaries of the femoral artery. Implicate in practicing the invention, is the recognition that the lower extremity arterial circulation lies close to the body surface (skin surface) and can provide easy access to peri cutaneous injections of botulinum toxin. The regions corresponding to easy access are 1. Femoral region corresponding to the area around the inguinal ligament (femoral artery) (See FIG. 4)
2. Popliteal region in the back of the knee (Popliteal artery). See FIG. 5.
3. Foot region instep (dorsum) and medial posterior tibial. (Corresponding to the posterior tibial artery). See FIG. 6.

Each of these areas may be injected individually or in combination depending on the extent, nature and location of the symptoms.

Documentation of peripheral arterial disease and impaired blood flow by be done clinically or in conjunction with diagnostic testing.

The above injection region are also unique in that the regions specified do not contain the muscular portion of many muscles involved in lower extremity movement. That is, the injection allows regional neurotoxin on large to intermediate size arteries effect without creating leg weakness.

The dose range is 5-15000 U dependent on immunotype used (A-G). For type A, preparations shall include pure neurotoxin preparations as well as complex (assessor protein containing preparations). Injections may be given under ultrasound control or by direct inspection. Injections may be multiple or single point in a given region. Doses may be confined to one or several regions.

Para spinal injections may be used in the lower back region to further access the par spinal sympathetic ganglia on the side of the symptoms.

EXAMPLE 1

62 year old nurse presented with severe pain right brow, forehead and scalp for the past year associated with progressive right sided enophthalmos over a 30 year period. The enophthalmos was associated with progressive hair loss over a linear region on the right portion of the scalp and atrophy over the right forehead and brow (see FIG. 1). The enophthalmos started at age 31 and resulted in a biopsy which showed focal inflammation in muscle and skin consistent with the diagnosis of linear scleroderma (En coup de Sabre) and Parry Romberg syndrome. There was no history of Reynaud's syndrome but complained of cold feet being a constant problem. There was no evidence of multisystem disease, systemic sclerosis or morphea skin lesions. The pain which had been at first intermittent became constant and rated as a 9 of 10 in severity causing inability to maintain gainful employment. Because pain was not relieve by systemic steroids, anti seizure medications or other oral analgesics, a trial of botulinum type A toxin injections were given over the forehead and scalp receiving 60 LD 50 units over six location on the afflicted side. Within two to three weeks, she noted progressive improvement of the pain decreasing in severity to a 1 of 10. Multiple injections with the same dose were given over the following year which sustained benefit. She felt the pain mitigate sufficiently after this period so not to require further botulinum treatment.

Four years prior to presentation she noted decrease in her short term memory and periods of amnesia causing her be unable to perform her duties as a post operative nurse. Workup demonstrated some degree of organic brain syndrome with short term memory loss and partial complex seizures. MRI imaging demonstrated multiple lesions within the right hemisphere and in temporal lobe cortex and periventricular regions. The lesions appeared multiple with slightly demyelization with blurred borders. Atrophy was noted in the temporal lobe both laterally and medially. She was started on Lamictal with control of temporal lobe epilepsy and however her memory remained impaired.

Because the prior injection was effected a decade earlier and because severe sharp constant pain, another empiric trial of botulinum toxin was given to the right scalp and brow region. She ranked the pain as variable but severe most of the time (10 of 10). Another trial of botulinum toxin was administered in multiple locations over the right frontal and temporal bone. She noted dramatic improvement pain and substantial improvement in her memory.

Because of progression of disease and concern as to cause of brain lesions, repeated MRA, MRS and MRP studies were conducted. MRA demonstrated diffuse narrowing of posterior branches of the middle cerebral artery on the side of hemifacial atrophy perfusing the temporal lobe. MRS showed abnormal lactate ratios within the right side of the temporal lobe. SPECT scan showed.

Because of improved results increased botulinum toxin dose over the right temporal bone (80 U), frontal bone (60 U, type A,) and occipital bone (60 U), was administered as well as a smaller dose over the right carotid artery (30 U). Remarkable improvement in pain, memory, well being and spontaneous thought ensued.

Comment: This patient with Parry Romberg syndrome demonstrated characteristic narrowing of vessels on MRA and evidence of metabolic damaged of the brain parenchyma on MRS study as well as temporal lobe atrophy in the distribution of brain perfused by the narrowed and impaired vessels. Injection of botulinum toxin improved pain in the injected region and improved higher cognitive status. The pain in this syndrome although similar to trigeminal neuralgia may represent an ischemic pain, consistent with evidence of ischemia as a cause of the pain. Although the cause of trigeminal neuralgia is unknown, the ischemic etiology is the most plausible primary cause considering know vascular pathology associated with the syndrome and vascular narrowing of cerebral vessels well demonstrated on MRA. The vasodilatory effect of botulinum toxin represents the essential critical effect improving the patients outcome.

The Parry Romberg syndrome pain has been characterized as a trigeminal like pain usually because of severity, unilateral location and associated with exaggeration by tactile stimulation. Because of associated fat, muscle and skin, an explanation as to the cause of pain as well as the facial dystrophy seems to be most likely ischemic, a cause which could also explain the facial dystrophy. If so, the vasodilatory effect of botulinum is a highly plausible mechanism for treating the pain and may hypothetically effect the progression of facial and scalp dystrophy.

We claim:

1. A method of increasing cerebral blood flow in a patient having impaired cerebral blood flow comprising the steps of:
   a. identifying a subject with an impairment of cerebral blood flow;
   b. injecting a botulinum toxin preparation within a defined dose range into the extra cranial region of the head or neck of said patient;
   c. allowing the botulinum toxin to spread within the deep brain structure and cause increased cerebral blood flow;
   d. thereby preventing progression of or enhancing recovery from the impaired cerebral blood flow.

2. The method of claim 1 in which the impairment of cerebral blood flow is stroke.

3. The method of claim 1 in which the cause of impaired cerebral blood flow is brain vascular bed development impairment.

4. The method of claim 3, wherein the brain vascular bed development impairment is hypoxic ischemic encephalopathy.

5. The method of claim 1 in which the impairment of cerebral blood flow is secondary to diabetes mellitus.

6. The method of claim 1 in which the impairment of cerebral blood flow is due to carotid artery disease.

7. The method of claim 1 in which impairment of cerebral blood flow is due to aneurysm.

8. The method of claim 1 in which impairment of cerebral blood flow is due to hypertension.

9. The method of claim 1 in which impairment of cerebral blood flow is due to Parry Rhomberg Syndrome.

10. A method of claim 1, further comprising the step of localizing treatment based on neuroimaging analysis.

11. The method of claim 10, in which the impairment of cerebral blood flow is stroke.

12. The method of claim 10, in which the cause of impaired cerebral blood flow is brain vascular bed development impairment.

13. The method of claim 12, wherein the brain vascular bed development impairment is hypoxic ischemic encephalopathy.

14. The method of claim 10, in which the impairment of cerebral blood flow is secondary to diabetes mellitus.

15. The method of claim 10, in which the impairment of cerebral blood flow is due to carotid artery disease.

16. The method of claim 10, in which impairment of cerebral blood flow is due to aneurysm.

17. The method of claim 10, in which impairment of cerebral blood flow is due to hypertension.

18. The method of claim 10, in which impairment of cerebral blood flow is due to Parry Rhomberg Syndrome.

* * * * *